United States Patent
Tatarek

(10) Patent No.: US 8,276,584 B2
(45) Date of Patent: Oct. 2, 2012

(54) CONSERVING DEVICE FOR BREATHABLE GAS

(75) Inventor: Andrew Richard Thomas Tatarek, Hampshire (GB)

(73) Assignee: Concept 2 Manufacture Design OCD Limited, Hampshire (GB)

( * ) Notice: Subject to any disclaimer, the term of this patent is extended or adjusted under 35 U.S.C. 154(b) by 1202 days.

(21) Appl. No.: 11/817,557

(22) PCT Filed: Mar. 2, 2006

(86) PCT No.: PCT/GB2006/050043
§ 371 (c)(1), (2), (4) Date: Feb. 29, 2008

(87) PCT Pub. No.: WO2006/092635
PCT Pub. Date: Sep. 8, 2006

(65) Prior Publication Data
US 2008/0190429 A1    Aug. 14, 2008

(30) Foreign Application Priority Data

Mar. 2, 2005 (GB) .................................. 0504223.9
Sep. 27, 2005 (GB) .................................. 0519620.9
Sep. 28, 2005 (GB) .................................. 0519729.8
Sep. 28, 2005 (GB) .................................. 0519730.6

(51) Int. Cl.
*A62B 9/02* (2006.01)
*A61M 16/00* (2006.01)

(52) U.S. Cl. ......... 128/204.23; 128/200.24; 128/204.18; 128/204.26; 128/205.18; 128/205.24

(58) Field of Classification Search ............. 128/200.24, 128/204.18, 204.21, 204.23, 204.26, 205.18, 128/205.24; 137/908; 251/30.01, 30.05
See application file for complete search history.

(56) References Cited

U.S. PATENT DOCUMENTS 4,054,133 A * 10/1977 Myers ....................... 128/204.26
(Continued)

FOREIGN PATENT DOCUMENTS

EP    1 028 770 A    8/2000
(Continued)

OTHER PUBLICATIONS

The Written Opinion for PCT Application No. PCT/GB2006/050043; Filed Mar. 2, 2006.
(Continued)

*Primary Examiner* — Annette Dixon
(74) *Attorney, Agent, or Firm* — Alston & Bird LLP

(57) ABSTRACT

A pneumatic oxygen conserving device for supplying oxygen to a user via a single-tube cannula is described. Inhalation is sensed by negative pressure in an output line 11 which causes a sensing valve 21 to open, thus venting a main control volume 14 via vent line 22. This fall in pressure causes a main control valve 2 to open to supply a pulse of gas. This pressurizes the output line 11 which in turn causes the sensing valve 21 to close, thus preventing further venting. Volume 14 now re-pressurizes via line 15 and restrictor 16 and eventually reaches a level at which valve 2 closes and terminates the pulse of gas supplied to the user. A sensing delay valve 35 is incorporated in the vent line 22 from volume 14 to prevent the volume from venting after the first pulse has been delivered, until after the user has finished inhaling.

17 Claims, 8 Drawing Sheets

U.S. PATENT DOCUMENTS

| | | | |
|---|---|---|---|
| 4,570,631 A | | 2/1986 | Durkan |
| 4,699,351 A | * | 10/1987 | Wells ............................ 251/29 |
| 4,706,664 A | * | 11/1987 | Snook et al. ............. 128/204.23 |
| 4,932,402 A | * | 6/1990 | Snook et al. ............. 128/204.23 |
| 5,099,836 A | * | 3/1992 | Rowland et al. ......... 128/204.23 |
| 5,603,315 A | * | 2/1997 | Sasso, Jr. ................. 128/204.18 |
| 6,237,594 B1 | * | 5/2001 | Davenport ............... 128/204.26 |
| 6,378,520 B1 | * | 4/2002 | Davenport ............... 128/204.26 |
| 6,427,690 B1 | | 8/2002 | McCombs et al. |
| 6,484,721 B1 | * | 11/2002 | Bliss ........................ 128/205.24 |
| 6,568,391 B1 | * | 5/2003 | Tatarek et al. ........... 128/204.26 |
| 7,191,780 B2 | * | 3/2007 | Faram ...................... 128/204.25 |
| 7,591,266 B2 | * | 9/2009 | Zaiser et al. ............. 128/205.24 |
| 7,708,016 B2 | * | 5/2010 | Zaiser et al. ............. 128/204.26 |
| 2004/0154620 A1 | | 8/2004 | Gale et al. |

FOREIGN PATENT DOCUMENTS

| | | |
|---|---|---|
| JP | 43-027716 | 11/1968 |
| JP | 11-506643 | 6/1999 |
| WO | WO 96/40336 | 12/1996 |
| WO | WO 99 22795 | 5/1999 |

OTHER PUBLICATIONS

International Search Report for PCT/GB2006/050043.

\* cited by examiner

-- Prior Art --

CONSERVING DEVICE FOR BREATHABLE GAS

CROSS-REFERENCE TO RELATED APPLICATIONS

This is a United States national stage application of international patent application PCT/GB2006/050043, filed Mar. 2, 2006, which international patent application was published under International Publication Number WO 2006/092635 A1 on Sep. 8, 2006. This patent application and said international patent application each claim the benefit of priority of each of: United Kingdom patent application GB 0504223.9, filed Mar. 2, 2005; United Kingdom patent application GB 0519620.9, filed Sep. 27, 2005; United Kingdom patent application GB 0519729.8, filed Sep. 28, 2005; and United Kingdom patent application GB 0519730.6, filed Sep. 28, 2005.

TECHNOLOGICAL FIELD

This invention relates to a pneumatic conserving device for breathable gas, primarily oxygen.

BACKGROUND OF THE INVENTION

Oxygen therapy is used to supplement the oxygen in the atmosphere in a variety of applications. Examples include:

(i) For people with damaged lung function—chronic obstructive pulmonary disease (COPD), emphysema or asthma.

(ii) For high altitudes, where the partial pressure of oxygen is too low for sustaining a person, e.g. the dropdown masks in aircraft, or devices used in high altitude climbing.

(iii) For general oxygen therapy, where an additional amount of oxygen has a therapeutic effect on the patient.

(iv) For use with a nebuliser, where it is an advantage to deliver only the amount of drug that can be absorbed by the patient.

Conventional devices for oxygen therapy give a constant flow, typically by metering the gas through a flow-meter or a fixed orifice. The oxygen is delivered to the patient typically via a nasal cannula—a tube connecting the outlet of the regulator, to the nostrils, or to a mask that covers the mouth and nose.

Oxygen conserving devices seek to improve on the conventional oxygen therapy devices by avoiding wastage of oxygen. An ideal oxygen conserving device would deliver gas for about half a second at the start of inhalation, then would not deliver any more until the start of the next inhalation. In this way only the gas that goes deep into the alveoli is consumed, and the oxygen that would otherwise be wasted (either delivered during exhalation, or just enter the air passages and trachea and be exhaled, not absorbed) and lost with the exhaled gas is instead conserved.

The advantages of conserving the oxygen in this way are well known, and include including making an oxygen cylinder or other supply last about three times as long, and increasing the travelling range of a person dependent on oxygen therapy. They may also reduce the number of cylinders a gas company has to deliver. There are also potential therapeutic benefits in comparison to constant flow devices, such as less drying of the nasal tissues.

A number of electronically controlled oxygen conserving devices exist on the market, which have the disadvantages of having to use batteries, temperature range limitations, and bulk—the designs tend to be difficult to incorporate into a pressure regulator as a single unit, and so end up being a separate unit, with the need for pressurised tubing between the regulator and the conserving device.

A fundamental problem that needs to be overcome in the design of a conserving device is that the resistance of the cannula to a typical therapy flow may be of the order of 100,000 Pa, whereas the pressure drop at the nose on inhalation may be typically 50 Pa. This means that once flow is started the pressure at the nose is too small to be detected at the device if a standard single tube cannula is used. It also means that transducers within the device capable of reading the approx 10-20 Pa of pressure needed to detect the start of an inhalation would be damaged by the pressure during flow.

The standard way to overcome this limitation is to utilise a dual lumen cannula—one tube for delivering the flow to the user, and a separate tube for transmitting the pressure at the user's nose to a sensing point on the conserving device. However, dual lumen cannulas are unpopular, because they are less easily available than the single lumen type, require two connections to be made instead of one, and are more expensive to make. They also mean that the user is restricted to a specific cannula, and cannot use the cannula that is most comfortable for them.

A number of pneumatically operated oxygen conserving devices exist on the market. The simplest type, described for example in U.S. Pat. No. 5,360,000 operates like a digital demand valve—giving a constant flow during inhalation, and switching off during exhalation. These have the disadvantage that the gas that is delivered after the start of the breath is wasted in the breathing passages and never gets to the alveoli.

FIG. 1 of the accompanying drawings shows a pneumatically operated oxygen conserving device which combines together common features from known single-tube cannula devices. Note that FIG. 1 is not intended to show a particular known device in detail, but to represent the main features of known devices, as they pertain to the present invention.

The device receives an oxygen supply to an inlet 1. Typical known devices operate from a supply pressure obtained for example from the output of a medical pipeline system or regulator, or from the output of a medical regulator—at a pressure typically from 1 to 5 bar according to the country and application. They may also operate directly from a liquid oxygen delivery system, typically regulated to a pressure of 1.5 bar.

The device may be incorporated into a high pressure regulator that uses gas from a cylinder and reduces it to the operating pressure of the conserving device.

Gas entering at inlet 1 passes via an input line 10, through a control valve 2 and via an output line 11 to an outlet 12 for connection to the single-tube cannula (not shown). The control valve is controlled, as represented by a control line 13, by the level of pressure in a main control volume 14. When the pressure in the main control volume is high (at a point approaching the level of the supply pressure), the flow is off, and when the pressure in the main control volume is low, the flow is on.

The main control volume is pressurised from the input line 10 via a flow line 15 in which is placed a flow restrictor 16. The flow through the restrictor 16 is set such that the pressure build up in the main control volume 14 from a "flow on" condition to a "flow off" condition is the time for which flow is required—i.e. the amount of time from the start of a breath to give the ideal dose of oxygen.

A variable restrictor (flow adjuster) 17 is fitted in the output line 11a, 11b, dividing the line into two sections 11a and 11b respectively upstream and downstream of the restrictor. The restrictor 17 may alternatively be fitted in the input line 10.

The purpose of restrictor 17 is to meter the amount of flow that is delivered during the "flow on" condition.

The device is triggered by negative pressure sensed in a sensing volume 18 connected via a sensing line 19 to the output line 11b. The level of pressure in the sensing volume 18 controls, as represented by the control line 20, a sensing valve 21, for example in the form of a diaphragm, which allows air from the main control volume 14 to vent, usually to atmosphere as illustrated, via a vent line 22. When the pressure in the main control volume drops to a sufficient level, the control valve 2 is opened to start flow to the patient. Immediately the control valve opens, the pressure in the sensing volume 18 rises, which closes the sensing valve 21 and stops the venting of the main control volume 14. From this moment, the pressure in the main control volume 14 goes up, fed from the input line 10 via the flow line 15 and restrictor 16, until the level of pressure in the main control volume 14 reaches a sufficient level to close the control valve 2 and cut off the flow to the outlet 12.

The fundamental problem now is that, as a result of the flow stopping, there is no longer an elevated pressure in the output line 11b to keep the sensing valve 21 closed. Therefore, if at this moment the patient is still inhaling, the sensing valve opens again, and the main control volume 14 vents, thus opening the control valve 2 again to deliver another pulse of oxygen. This second pulse of oxygen is likely to mainly go to waste, because it is not required, as discussed above.

These difficulties are recognised in the prior art, and various ways of overcoming them have been described. For example, in EP 1028770, the flow adjuster is provided just after the gas inlet and a reservoir volume is provided between this and the main control valve. The control valve flows are set smaller than the flow required, and the pressure in the volume builds up during exhalation, and gets delivered at the start of inhalation. The amount of gas delivered on subsequent pulses and wasted is therefore less than the amount that would be delivered without the reservoir in place. However, there is still significant wastage, because the second and subsequent pulses contain a significant amount of gas.

In U.S. Pat. No. 6,484,721, use is made of a tail of gas flow after the initial pulse in order to prevent the occurrence of a second pulse during the same inhalation period. However, in order to be effective, a not insignificant amount of gas has to be used, which is wasted. The end of the tail of flow is undefined, so does not give a clear end point where sensing is definitely on or off, but depends on the level of the patient's breath.

BRIEF SUMMARY OF THE INVENTION

The present invention seeks to provide a pneumatic conserving device for breathable gas, the device having an outlet for connection to a cannula, and being operable to supply a pulse of gas at the beginning of inhalation, and no further gas until the beginning of the next inhalation.

According to the invention there is provided a pneumatic conserving device for breathable gas, the device comprising a main control valve connected in a user supply line between an inlet for receiving a supply of breathable gas and an outlet for connection to a user, main valve timer means for controlling the opening and closing of the main control valve, and sensing means for triggering the main valve timer means to open the main control valve upon sensing inhalation by the user, and to deliver a pulse of gas of predetermined duration to the outlet, the device being characterised by means for inhibiting operation of the sensing means, and delay timer means for controlling the inhibiting means to inhibit operating of the sensing means for a predetermined period following the delivery of the pulse of gas to the outlet.

Thus, once the pulse of gas has been delivered to the outlet, and hence to the patient, operation of the sensing means is inhibited so that it is unable to reactuate the main control valve to supply another pulse. Generally speaking the main valve timer means will be such as to keep the main control valve open, typically for about half a second, this period being known to provide sufficient gas to the user in normal circumstances. However, the period could be changed, as needed to suit the application. Following delivery of the pulse of gas, the sensing means is inhibited for said predetermined period in order to prevent further gas flow. This predetermined period may be set to start and end at various different times, but should at least include that part of the expected inhalation of the user which follows the end of the pulse of gas. In the preferred embodiment, the predetermined period starts at the termination of the pulse, and terminates at a time after the end of the inhalation period which caused the delivery of the pulse of gas, but before the commencement of the next inhalation period—in other words, at a time during exhalation. If the predetermined period commences at the time that the main control valve closes to terminate the delivered pulse of gas to the user, then the predetermined period is likely to be typically about 1.5 seconds.

In the preferred embodiment, the outlet is connected to a single tube cannula which passes the gas to the user. The sensing means is connected to the user supply line, downstream of the main control valve, in order to sense inhalation by the user, somewhat in the manner illustrated in FIG. 1. However, a twin-tube cannula may also be used, in which case the outlet is connected to one of the tubes, while the sensing means is connected to the other tube in order to sense inhalation by the user. For simplicity, the first (preferred) option will be assumed throughout the present specification.

The means for inhibiting operation of the sensing means can act on the sensing means in various different ways. In some of these ways, the sensing means is allowed to continue to sense for inhalation, but its output is prevented from acting on the main control valve timer means. In others the output of the sensing means is not prevented, but the operation of the sensing means itself is prevented, either by preventing it from sensing inhalation or by physically preventing operation of the sensing means.

Thus, in a first embodiment, a connection is provided between the sensing means and the main valve timer means to enable triggering of the main valve timer means upon sensing inhalation by the user. The inhibiting means comprises means for interrupting the connection, the interrupting means being controlled by the delay timer means to prevent triggering of the main valve timer means during the predetermined period.

In a second embodiment, the sensing means is connected to the user supply line for sensing the negative pressure due to inhalation, via a sensing delay valve forming part of the inhibiting means, and the delay timer means controls the sensing delay valve to remain closed for the predetermined period, thus preventing the sensing means from operating. Preferably the sensing means further includes a sensing volume connected to the user supply line and control means for opening the sensing valve when the pressure in said sensing volume is negative (indicating that the user is inhaling), and the sensing delay valve is connected between the user supply line and the sensing volume so that, when closed, the sensing delay valve prevents the sensing valve from sensing the pressure in the user supply line.

In a third embodiment, the sensing means is connected to the user supply line for sensing the negative pressure due to inhalation, and includes a moveable member such as a piston or diaphragm which moves in response to the negative pressure. The inhibiting means includes an inhibiting member for preventing or limiting movement of the moveable member during the predetermined period. The sensing means may, for example, comprise a sensing valve having a piston or diaphragm for sensing the inhalation pressure, the piston or diaphragm being mechanically connected to a valve member acting on a valve seat to close or open the valve. In this case, either the piston/diaphragm or the valve member could comprise the moveable member referred to above, and the inhibiting member is moveable between a first position in which it prevents operation of the sensing valve and a second position in which it does not prevent operation of the sensing valve. Thus, during the predetermined period, the inhibiting member is arranged to be in its first position, thus inhibiting operation of the sensing means.

One or both of the main valve timer means and the delay timer means may comprise a closed volume having pressurising means for pressurising the volume and vent means for venting the volume. In each case the volume further comprises a moveable member such as a piston or diaphragm which moves in accordance with the level of pressure in the volume and thereby acts to control either the main control valve (in the case of the main valve timer means), or the inhibiting means (in the case of the delay timer means). The timer function is achieved by incorporating a flow restrictor either in the pressurising means or the vent means, or both.

In the preferred embodiments, the timer function of the main valve timer means is realised by fitting a flow restrictor in the pressurising supply to the volume, and allowing free venting. Thus, the volume pressurises relatively slowly, preferably from the supply, over a controlled period roughly corresponding to the period of the delivery pulse, but vents relatively quickly. Control of the vent means by the sensing means can thus be used to trigger the commencement of the delivery pulse upon the detection of inhalation by the sensing means (provided, of course, that operation of the sensing means is not inhibited, as described above).

In the preferred embodiments, the timer function of the delay timer means is realised by fitting a flow restrictor in the vent means, but allowing a free flow of gas into the volume to pressurise it. Local conditions may require that the volume is pressurised via a one-way valve in order to prevent venting of the volume back into the supply in the event that the supply pressure to the volume drops. This arrangement enables the volume to quickly pressurise from the output of the main control valve during the delivery pulse. Once the delivery pulse has ended, the pressure level in the volume slowly vents, due to the restrictor in the vent means, over a period roughly corresponding to the predetermined period. During this period the moveable member in the volume controls the inhibiting means to prevent operation of the sensing means, as described above. As the pressure level in the volume falls, the moveable member eventually causes the inhibiting means to allow operation of the sensing means again, this being timed to be prior to the commencement of the next inhalation period, the beginning of which can thus be sensed in the normal way by the sensing means.

In the preferred embodiments of the invention the sensing means comprises a sensing valve connected in the vent means of the volume controlling the main control valve (hereinafter referred to as the main volume). The sensing valve is connected such that, when open, the main volume vents relatively quickly. In the normal sequence of operation, the main volume is maintained at supply pressure by being connected to the supply via the restrictor. As soon as the sensing valve detects the commencement of inhalation by the user, the valve switches from its normally closed position to an open position, thus rapidly venting the main volume. The level of pressure in the volume falls until, at some predetermined pressure, typically about 10% of the supply pressure, the main valve opens, thus commencing the pulse of gas for delivery to the user. As in the prior art devices, the absence of negative pressure, or the pressurisation of the outlet connection, causes the sensing valve to close thus preventing further venting of the main volume. The volume thus starts to fill again from the supply, ready for the commencement of the next inhale/exhale cycle, via the restrictor. When the pressure in the main volume reaches a predetermined level the main control valve is closed, and remains so for the rest of that inhale/exhale cycle.

BRIEF DESCRIPTION OF SEVERAL VIEWS OF THE DRAWING(S)

In order that the invention may be better understood, several embodiments thereof will now be described by way of example only and with reference to the accompanying drawings in which.

DETAILED DESCRIPTION OF THE INVENTION

Figure 1:
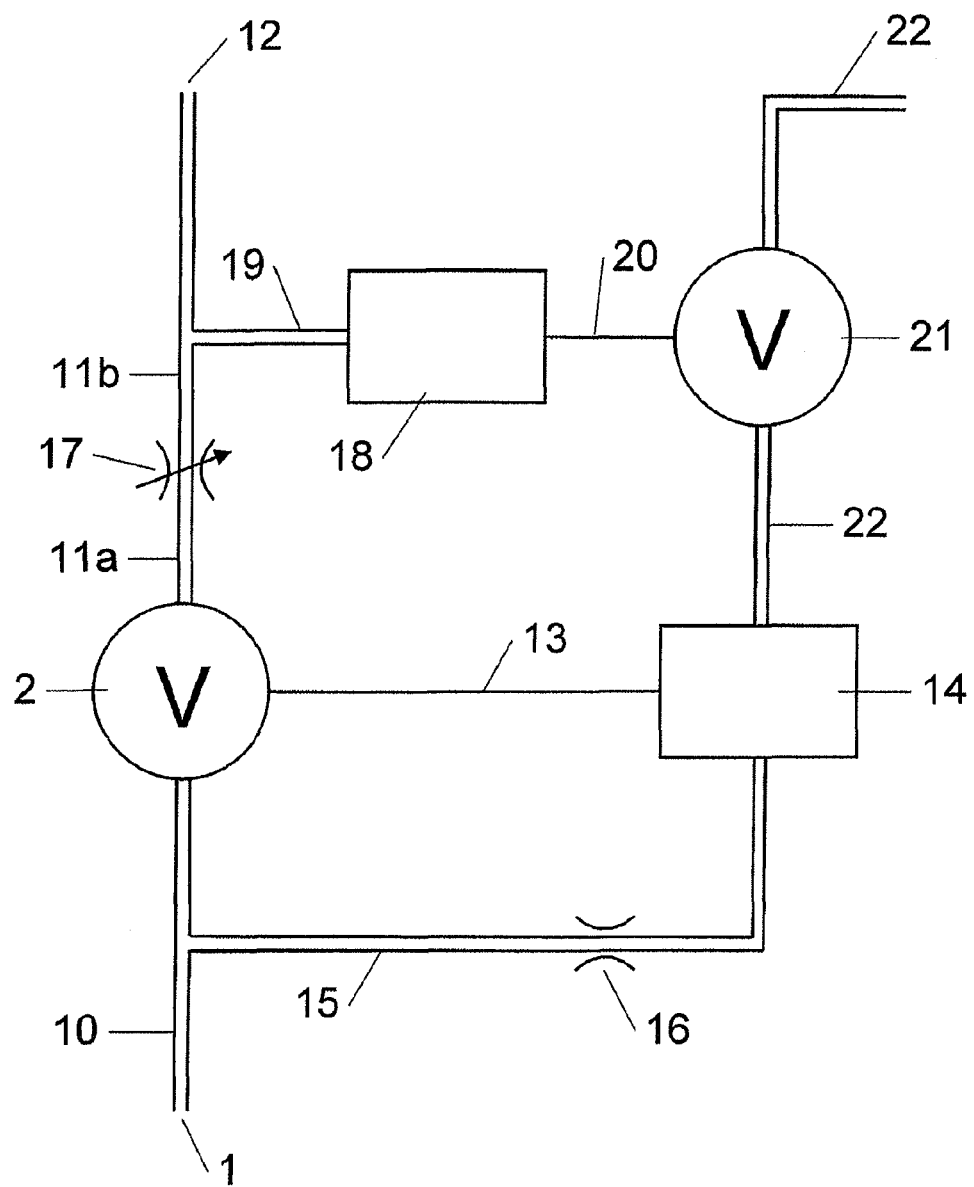
FIG. 1 is a block diagram of a representative known oxygen conserving device.

Throughout the drawings the same reference numerals are used where appropriate. Also, it should be noted that, in the following description, the values of 10% and 90% of supply pressure are quoted as the trigger points for operation of the valves. However, these are merely typical values given by way of example. In practice, 10% is in effect an abbreviation for a pressure just above zero (atmospheric) and 90% is a pressure just below the supply pressure. The actual values will depend upon the circumstances and in particular on the design of the valve elements.

The basic components of the oxygen conserving device illustrated in FIG. 2 operate in a similar way to that already described with reference to FIG. 1. The flow restrictor 16 is adjusted so that main control volume 14 fills from 10 to 90% of the supply pressure in the desired duration of the time for which the main control valve 2 is to be open—in other words, the pulse duration. The valve itself is normally closed and remains so when the pressure in the main control volume is greater than 10% of the supply pressure. The valve is set such that it closes when the pressure in the main control volume 14 rises above 90% of the supply pressure, and such that it opens when the pressure in the main control volume falls to less than 10% of the supply pressure. Likewise the sensing valve 21 is normally closed and remains so when the pressure in the section 11b of output line 11 is at or above zero. If, however, the pressure in line 11b, and hence sensing volume 18, drops by greater than a predetermined amount in a negative direction, corresponding to the action of inhalation by the user, the sensing valve 21 will open. Typically the supply pressure is between 1 and 5 bar, depending upon the application.

Branching off the section 11a of output line 11 is a line 30 including a one-way valve 31 connecting to a sensing delay volume 32. The valve 31 is such as to allow pressurising of the volume from the line 11a, but not flow in the reverse direction. The volume is vented by a vent line 33 including a flow restrictor 34. the vent line may vent to atmosphere, or to some other suitable point, for example, the output line 11b. The drawing illustrates a vent to atmosphere.

The restrictor 34 is set such that the time taken for the volume 32 to vent from supply pressure to 10% of supply pressure is roughly the same as the aforementioned predetermined period—in other words, the period from the termination of the delivery pulse of gas to the outlet 12 to a point in time during the subsequent exhalation.

The level of pressure in the sensing delay volume 32 controls the operation of a sensing delay valve 35 which is connected in the vent line 22, 22b, 22c, from main control volume 14, thus dividing the vent line into a first section 22a between the volume 14 and the valve 35 and a second section 22b between the valve 35 and the sensing valve 21. The valve 35 is normally open, corresponding to the situation in which the pressure in the sensing delay volume 32 is less than 10% of the supply pressure. The valve is set such that it closes when the pressure in the sensing delay volume rises above 10% of supply pressure.

The operation of the oxygen conserving device illustrated in FIG. 2 will now be described. For the purpose of the following explanation, it is assumed that a user is connected via a single-tube cannula (not shown) to the outlet 12 and that the user's breathing proceeds in a sequence of inhalation, followed by exhalation, cycles.

Immediately prior to the commencement of each inhalation, the situation can be summarised as follows:

(1) The pressure in the main control volume 14 is at supply pressure, the volume having pressurised during the previous cycle via the line 15 restrictor 16. The main control valve 2 is thus closed, and no gas is passing to the user.

(2) The pressure in the sensing delay volume 32 is at zero, the volume having vented during the previous cycle via the vent line 33 and restrictor 34. The sensing delay valve 35 is thus in its normally open state.

(3) The pressure in the sensing volume 18 is at zero and the sensing valve is accordingly in its normally closed state, thus preventing any venting from the main control volume 14.

As the user finishes exhaling and begins to inhale, a negative pressure is passed via the cannula to the output line 11b. This results in the following actions:

(1) The negative pressure in line 11b is transmitted via line 19 to sensing volume 18 and sensing valve 21 is thus opened.

(2) The sensing delay valve 35 remains open because the pressure in the sensing delay volume 32 is not changed, since there is no significant pressure in the line 11a to go through the one-way valve 31.

(3) The main control volume 14 rapidly vents via line 22 and valves 35 and 21, and the pressure level in the main control volume thus falls rapidly.

(4) When the pressure in the main control volume has fallen to less than 10% of the supply pressure, the main control valve 2 is opened. This pressurises the output line 11 and thus supplies breathing gas to the user via the valve 17, outlet 12 and the attached cannula. It will be noted that the variable restrictor (flow metering valve) 17 is positioned in the output line 11 downstream of the line 30. The open area of valve 2 needs to be larger than the largest setting of valve 17 so that, at this moment, the pressure in line 11a, becomes substantially equal to the supply pressure.

(5) The pressure in the output line 11a is transmitted to the sensing delay volume 32 via the line 30 and one-way valve 31, thus pressurising the volume 32. When the pressure in the volume 32 rises above 90% of the supply pressure, the sensing delay valve 35 closes, thus inhibiting operation of the sensing valve 21 by, isolating it beyond the now-closed delay valve 35 for as long as the sensing delay valve 35 remains closed, further venting of the main control volume is prevented, irrespective of whether the sensing valve 21 is open or closed. In practice an extra flow restrictor 36 may be necessary in the line 30 to slow down the pressurisation of the volume 32 to ensure that the sensing delay valve 35 closes after the sensing valve 21 (which, as noted below, also closes at this time) to ensure that the sensing valve 21 does not close until the main control volume 14 is fully vented.

(6) The pressure in the output line 11b is transmitted to the sensing volume 18 and thus closes the sensing valve 21. This has no effect at this time, because venting of the main control volume is already prevented by closure of the sensing delay valve 35, as described in step (5) above.

(7) The main control volume 14 will pressurise via the line 15 whenever the pressure in the volume is less than that in input line 10—i.e. the supply pressure. However, during venting of the volume, although the volume is filling through the line 10, the existence of the restrictor 16 ensures that the filling via line 15 is at a much slower rate than the venting via line 22a, 22b, 22c. With the venting now stopped, as a result of closure of sensing delay valve 35, the main control volume 14 begins to re-pressurise via the line 15. The rate of re-pressurisation is controlled by the restrictor 16 so as to keep the main control valve 2 open for a time sufficient to supply to the user a sufficient amount of gas for the present inhalation.

(8) When the pressure level in the main control volume reaches 90% of the supply pressure, via the line 15 and restrictor 16, the main control valve closes, thus terminating the supply of gas to the output line 11, and hence to the user. The exact width of the pulse of gas supplied to the user is set by the restrictor 16 and depends upon the circumstances. Typically the pulse width will be approximately 0.5 seconds.

(9) When the main control valve 2 closes, the pressure in output line 11 falls and if, as is likely, the user is still inhaling, the pressure line 11 will go negative again.

(10) The negative pressure in line 11 prevents further flow into the sensing delay volume 32 via the one-way valve 31 and the pressure in the volume thus starts to fall, due to venting via the vent line 33 and restrictor 34. In practice the volume 32 will be venting whenever its pressure is above atmospheric but, during the period when the main control valve 2 is open, and the output line 11 thus pressurised to supply pressure, the flow through the line 30 and valve 31 is great enough to overcome the venting via the restrictor 34, and the volume is thus able to pressurise quickly. Although the pressure in the volume 32 is falling, it remains high enough, for a time, to keep the sensing delay valve 35 closed.

(11) The negative pressure in line 11 is also transmitted to the sensing volume 18 and causes the sensing valve 21 to open. However, this has no practical effect, because the sensing delay valve 35 remains closed, as described in step (10) above, thus continuing to isolate the sensing valve, and preventing venting of the main control volume 14. This in turn prevents premature opening of the main control valve 2, and no further gas is thus supplied to the user.

(12) The condition of the components now remains static until the pressure in sensing delay volume 32 has fallen to less than 10% of supply pressure at which point the sensing delay valve 35 opens again. The time taken for this to occur is determined by the restrictor 34, which is set so that the valve 35 opens at a point after the end of inhalation by the user, and during the subsequent exhalation. Once the valve 35 is opened, the sensing valve 21 is no longer isolated, and is therefore ready to sense the commencement of the next inhalation by the user. During exhalation, the pressure in output line 11 is close to zero but, if anything, is slightly positive—typically about 50 Pa—which helps to keep the sensing valve 21 closed, and has no effect on either of valves 2 or 35.

(13) The condition of the components is now as described at the beginning, ready for the commencement of the next inhalation.

In summary, it will be seen that, during the period following the termination of the pulse of gas delivered to the user, and while the user is still inhaling, the sensing delay valve 35 remains closed, thus preventing the sensing valve 21 from venting the main control volume 14 and in turn preventing the main control valve 2 from opening again during inhalation. The operation of the device thus approaches the theoretical ideal, discussed above, of supplying just a single pulse of gas to the user at the beginning of inhalation, and nothing further until the next inhalation.

Figure 2:
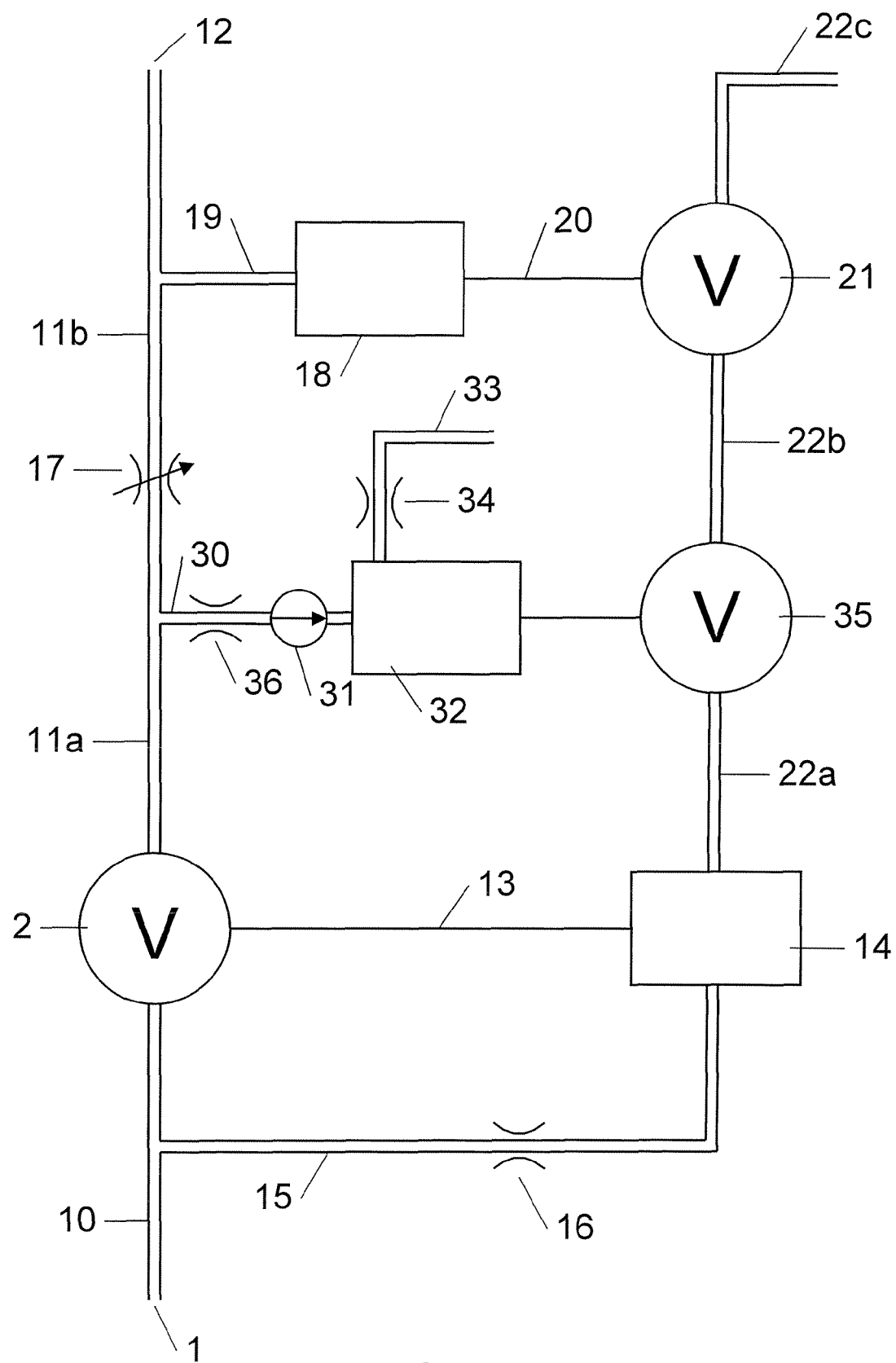
FIG. 2 is a block diagram of a first embodiment of an oxygen conserving device according to the invention.
Figure 3:
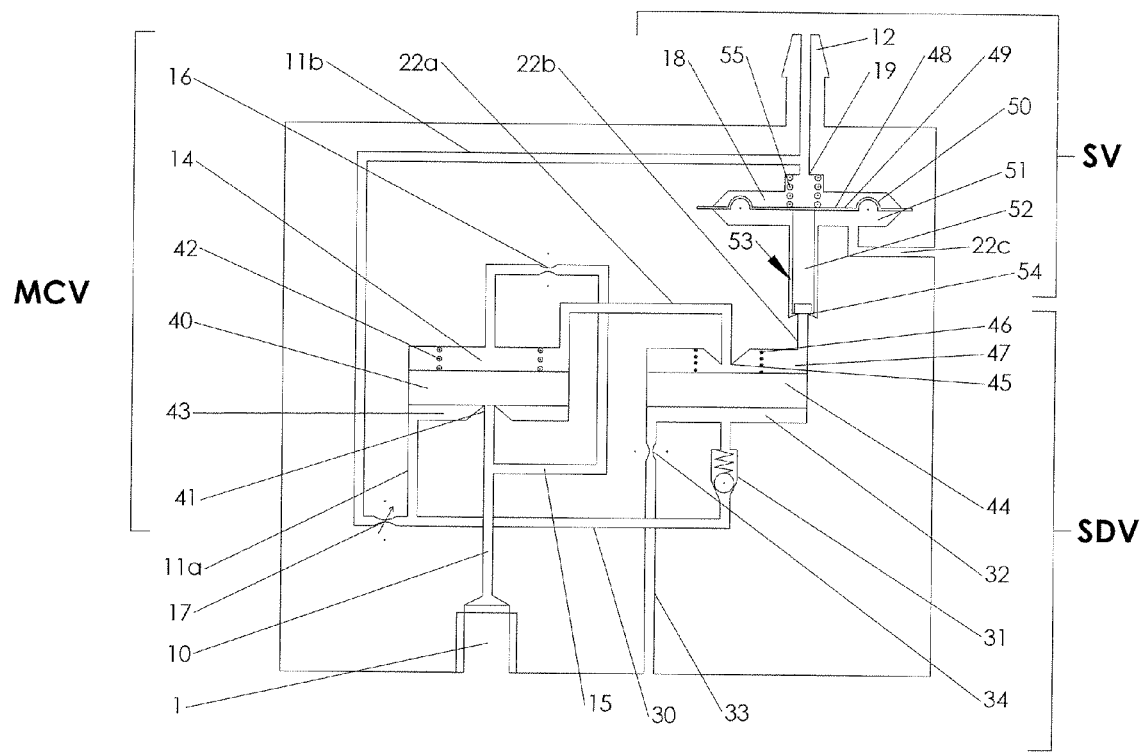
FIG. 3 is a more detailed pneumatic circuit diagram illustrating one way of implementing the embodiment of FIG. 2.

Reference is now made to FIG. 3 which shows in more detail an embodiment of the invention which operates in the manner described with reference to FIG. 2. For clarity, and to save on explanation, the corresponding parts have been given the same reference numerals as in FIG. 2. The letters MCV in FIG. 3 stand for "main control valve" and the corresponding bracket encloses the individual components of the main control valve, and the main control volume. The same applies to the sensing delay valve SDV and the sensing valve SV.

Although laid out differently, the above detailed explanation of FIGS. 1 and 2 should enable the detail of FIG. 3 to be ascertained. The main addition is that the valves are shown in greater detail to illustrate a practical embodiment of the FIG. 2 device.

The flow metering valve 17 is represented by a standard symbol since it is known technology; for example, the valve could comprise a selectable range of fixed orifices, or a needle valve with a means for the user to adjust the flow delivered during the pulse, together preferably with means for displaying the setting. The flow rate may be typically adjusted in the range 0.1 to 20 L/min, but it may be smaller or larger, depending upon the application.

The main control valve 2 comprises a main control diaphragm 40 which comprises a disk of elastomeric material biased against a main control valve jet 41 either by a spring 42 or by rubber (not shown) being located with the outside diameter lower, in the direction as illustrated, than the top of the jet 41, such that the tension of the rubber urges the centre of the diaphragm 40 against the jet 41. The diaphragm moves in a cylinder which is divided by the diaphragm into an upper chamber—the main control volume 14—and a lower chamber 43. The outside diameter of the diaphragm 40 is sealed against the walls of the cylinder in which it is located. It will be understood that the diaphragm 40 could be replaced by a variety of equivalent means, such as a piston with one or more o-rings.

The exact thickness and shape of the diaphragm 40 and spring 42 are adjusted so that the forces acting and the stiffness of the parts are such that a pressure of over 10% of the supply pressure in the main control volume 14 is enough to overcome the supply pressure acting on the sealing area of the jet 41 and make the diaphragm 40 seal against the jet 41.

As already mentioned, the restrictor 16 is of a size that the time taken for the main control volume 14 to pressurise from 10% to 90% of the supply pressure corresponds to the time required for the duration of the pulse of gas delivered to the user at the onset of inhalation. This duration is typically 0.5 seconds.

The sensing delay valve 35 is of similar construction and comprises a sensing delay diaphragm 44 which is biased away from a sensing delay valve jet 45 either by a spring 46 or by rubber being located with the outside lower, in the direction as illustrated, than the top of the jet 45.

The diaphragm moves within a cylinder to thus define an upper chamber 47 and a lower chamber—the sensing delay volume 32. The outside diameter of the diaphragm 44 is sealed against the walls of the cylinder in which it is located. As before, the diaphragm could be replaced by a variety of other means, such as a piston with one or more o-rings.

The exact thickness and shape of the diaphragm 44 and spring 46 are arranged such that when the pressure in the sensing delay control volume 42 is above 10% of the supply pressure, and the pressure around the jet 45 is close to atmospheric, the diaphragm 44 will be urged towards the jet 45, thus preventing flow through it.

While the main control valve 2 is open, the line 30 is at supply pressure, because the main control valve, when open, is a large orifice compared to the flow metering valve 17. The sensing delay control volume 32 will thus preferentially fill via the channel 30 and through the relatively unrestricted one-way valve 31.

As already mentioned, the sensing delay control volume 32 is vented through a restrictor 34 set such that the time to vent the control volume 32 from supply pressure to 10% of the supply pressure is long enough to end after the user has finished inhaling, but before the start of the next inhalation. Venting of the sensing delay control volume 32 could be to atmosphere, as shown, or could be to the line 30, or the output line 11.

The sensing valve 21 comprises a very light diaphragm 48 sealing across a chamber. The diaphragm 48 advantageously comprises a relatively stiff centre portion 49 and a resilient portion 50 around the outside which allows the stiff portion 49 to move freely perpendicular to its face. The diaphragm 48 divides the chamber into an upper volume—the sensing volume 18—and a lower volume 51 which is vented to atmosphere via the vent line 22c.

The diaphragm acts on a valve member 52 which is moveable vertically in a narrow bore 53 and has, at its lower end, a seal which bears against a sensing valve jet 54. Other methods of sealing the jet will be apparent to those skilled in the art.

The diaphragm 48 is biased towards the jet 54 by means of a spring 55, or equivalent. The spring is such as to bias the valve stem 52 against the jet 54 by a force sufficient to overcome the force of the supply pressure acting over the area of the jet 54. If there is low or zero pressure difference across the diaphragm 48, the spring 55 will act to urge the valve stem 52 against the jet thus creating a seal and preventing flow from the vent line 22c to atmosphere. However, if the pressure difference is such that the pressure on the user side is negative compared to the atmospheric pressure by enough to overcome the stiffness of the spring 55 and/or diaphragm 48, the diaphragm 48 will move upwards to thus allow the sealing member to be moved away from the jet by the pressure within line 22b, thus breaking the seal and allowing the gas in line 22b to vent to atmosphere via line 22c. This is termed the "cracking pressure" and, in oxygen therapy applications, is likely to be in the order of 10 Pa to 20 Pa.

The small forces involved in the operation of the sensing valve 21 mean that its diaphragm 48 has to be relatively light. In addition, the jet 54 has to be small and the valve stem 52 has to seal against the jet with a relatively small force.

During operation of the device, and when the main control valve 2 is open to supply the pulse of gas to the user, a high pressure develops in the output line 11 due to the resistance of the cannula to therapy flow. This high pressure is directly applied to the diaphragm 48 which therefore has to be constructed and/or mounted in such a way as to withstand the forces applied to it due to this pressure. The pressure could, for example, result in the centre portion 49 collapsing.

In an alternative construction (not shown) the sensing jet could be positioned directly under diaphragm with a resilient disk mounted on the diaphragm to seal against it. However, there are known issues in such a construction due to leakage as a result of the diaphragm not moving squarely to the jet. A finite length of engagement, such as in the construction illustrated, improves the chance that the sealing member, in whatever form it takes, is presented squarely to the jet, thus reducing the force required to effect a seal.

Another design consideration is that the volume downstream of the sensing delay jet 45, namely the vent line 22b and volume 47 has to be small in relation to that upstream of the jet, namely vent line 22a and volume 14. The reason for this is that there are conditions in which the downstream volume is empty and the sensing delay valve will open. At this stage, it is important that the pressure drop in the main control volume 14, caused by the equalisation of the volumes 14 and 32, is not sufficient to cause the main control valve 2 to open, and thus start gas flow.

A further design consideration is that the open area of the sensing jet 54 has to be large compared to the restrictor 16 which feeds the main control volume so that the pressure from the combination of the main control volume 14, vent lines 21a and 21b, and chamber 47 can be vented almost instantaneously as the valve stem 52 moves away from the jet 54.

For ease of understanding, the main stages of operation of the valve of FIG. 3 are shown in the attached Table including the pressures and valve states at each stage of the inhalation/exhalation cycle. The numbers in the left-hand column represent stages in the progress of operation, and have no particular significance. The quoted percentages refer to percentages of the supply pressure.

TABLE 1

| No | Stage | Typ Time (s) | Pressures in the Volumes as Labelled in the Drawing FIG. 3 | | | | State of Valves | | | Flow To User |
|---|---|---|---|---|---|---|---|---|---|---|
| | | | 43 | 14 | 32 | 18 | 47 | MCV | SDV | SV | |
| 1 | Ready state | — | 0 | 100% | 0 | 0 | 100% | Closed | open | closed | 0 |
| 2 | Start inhale | 0 | 0 | 100% falling rapidly | 0 | ~−60 Pa | 100%, falling rapidly | Closed | open | open | 0 |
| 3 | Pressure in 14 has fallen, MCV opens | 0.02 | Rising quickly to 100% | 10% or below | 0, rising quickly to 100% | Rising quickly to ~+10,000 Pa | as 14 | Open | open, closing rapidly | open, closing rapidly | Flow |
| 4 | SV & SDV have shut | 0.05 | 100% | 10% rising | Rising | ~+10,000 Pa | 10% rising | Open | closed | closed | Flow |
| 5 | MCV just closing | 0.55 | 100% Falling | 90% rising | 100% | ~+10,000 Pa falling | ~10% | Closing | closed | closed | Flow, falling |
| 6 | MCV just closed | 0.58 | Falling to 0 quickly | Rising to 100% | 100%, falling | Falling to 0 quickly | ~10% | Closed | closed | closed | 0 |
| 7 | User still inhaling after stage 6 | 0.60 | 0 | 100% | Falling | ~−60 Pa | Falling to zero quickly | Closed | closed | open | 0 |
| 8 | SDV opens | 2 | 0 | Rising to 100% | 0 | + few mm H$_2$O | 0 | Closed | open | closed | 0 |
| 9 | Back to stage 1 | | 0 | 100% | 0 | 0 | 100% | Closed | open | closed | 0 |

As has been made clear, one of the purposes of the present invention, and its associated designs, is to avoid wastage of oxygen. Careful dimensioning of the chambers and passages can help to minimise this wastage. For example, the combination of the main control volume 14, the vent line 22, 22b, 22c and the chamber 47 is vented to atmosphere during each breath and therefore the lower the size of these components, the lower will be the wastage. Similarly, the sensing delay control volume 32 is vented at each breath and although, as mentioned above, this volume can be emptied into the user line, the venting occurs at a time during which the flow is wasted anyway. Therefore, once again, the smaller this volume can be made, the better.

Figure 4:
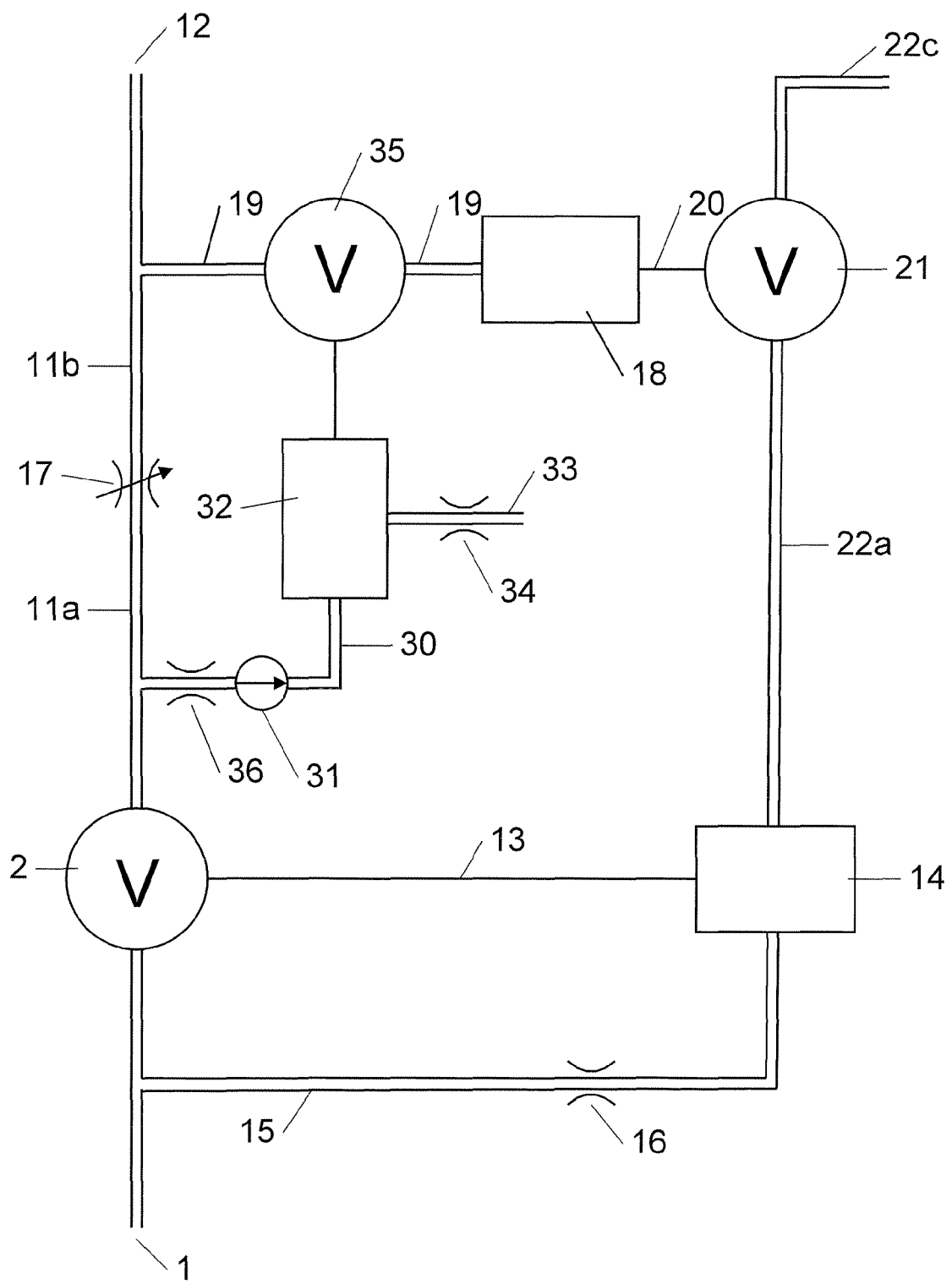
FIG. 4 is a block diagram of a second embodiment of an oxygen conserving device according to the invention.

Reference is now made to FIG. 4 which shows a second embodiment of the invention.

The only difference between the embodiment of FIG. 4 and that of FIG. 2 is that the normally-open sensing delay valve 35 is placed in the line 19 connecting the output line 11b to the sensing volume 18, instead of in the vent line 22. Thus, instead of inhibiting operation of the sensing valve 21 by isolating it from the vent line 22a of the main control volume 14, as in the embodiment of FIG. 2, the operation of the sensing valve is inhibited by cutting off its input from the output line 11b. Only when the valve 35 is open can the pressure in line 19 be communicated to the volume 18. When the valve 35 is closed, the sensing volume 18 becomes isolated, and simply retains the same pressure, subject to leakage, that it had at the moment that the valve 35 closed.

The operation of the device of FIG. 4 will be largely apparent from the previous description of FIG. 2, and only the differences will be highlighted.

Immediately prior to each inhalation, the valve 35 will be open so that the drop in pressure in output line 11*b* is sensed by the sensing valve in the normal way, via the line 19, valve 35 and sensing volume 18. Operation continues substantially as described above until the beginning of the pulse of gas delivered to the user causes the pressure in the output line 11 to rise to supply pressure. This in turn causes the pressure in sensing delay volume 32 to rise, via line 30 and one-way valve 31, until it reaches 90% of supply pressure, at which point the sensing delay valve 35 closes, thus isolating the sensing volume 18 from the output line 11*b*.

At the termination of the pulse of gas delivered to be user, the pressure in output line 11*a* falls, as before, and this starts the process of venting the sensing delay volume via line 33 and restrictor 34. Eventually, during the subsequent exhalation, the pressure falls to a sufficient extent to open the valve 35 once more, and "re-connect" the sensing volume 18 to the output line 11*b*. In the meantime, and in particular during the remainder of the inhalation, the sensing volume 18 remains isolated by the closed valve 35, and the sensing valve 21 therefore remains closed, thus preventing the main control volume 14 from venting.

Figure 5:
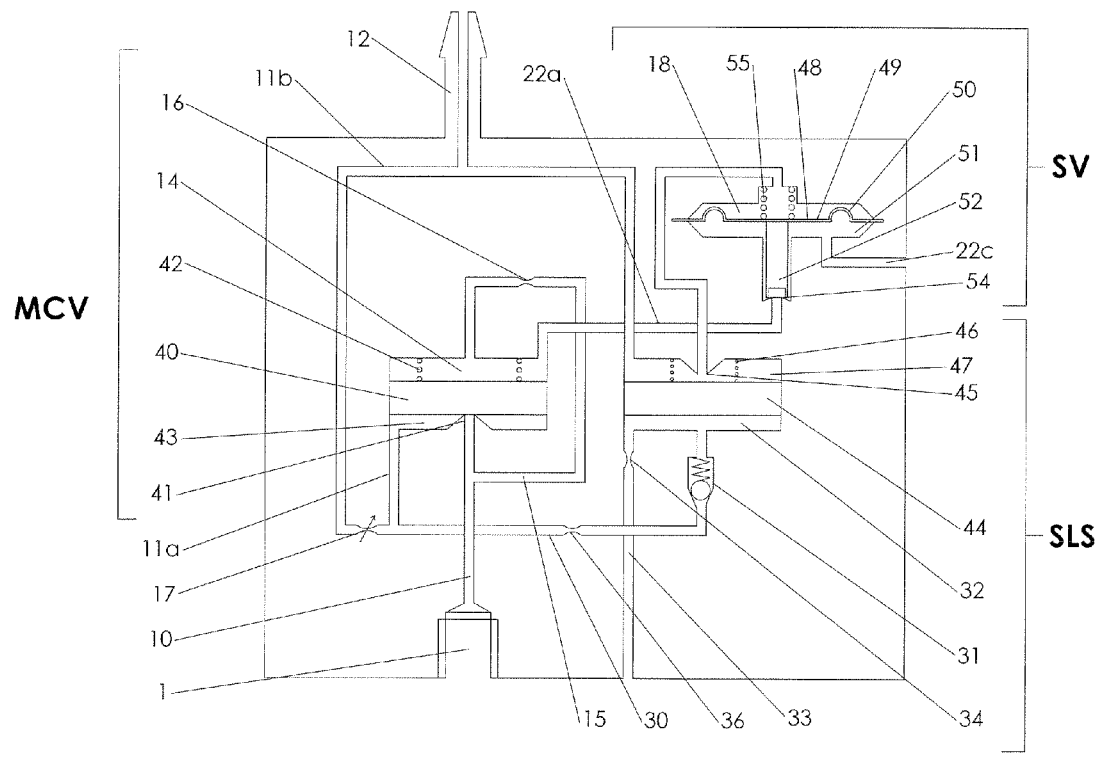
FIG. 5 is a more detailed pneumatic circuit diagram illustrating one way of implementing the embodiment of FIG. 4.

FIG. 5 is similar to FIG. 3 and shows a more detailed practical embodiment of the device of FIG. 4. The construction and operation of the embodiment of FIG. 5 will be fully understood from the previous explanations. The following table summarises the sequence of operation of the device of FIG. 5, and gives the pressures and valve states at each stage. As before the quoted percentages refer to percentages of the supply pressure.

Figure 6:
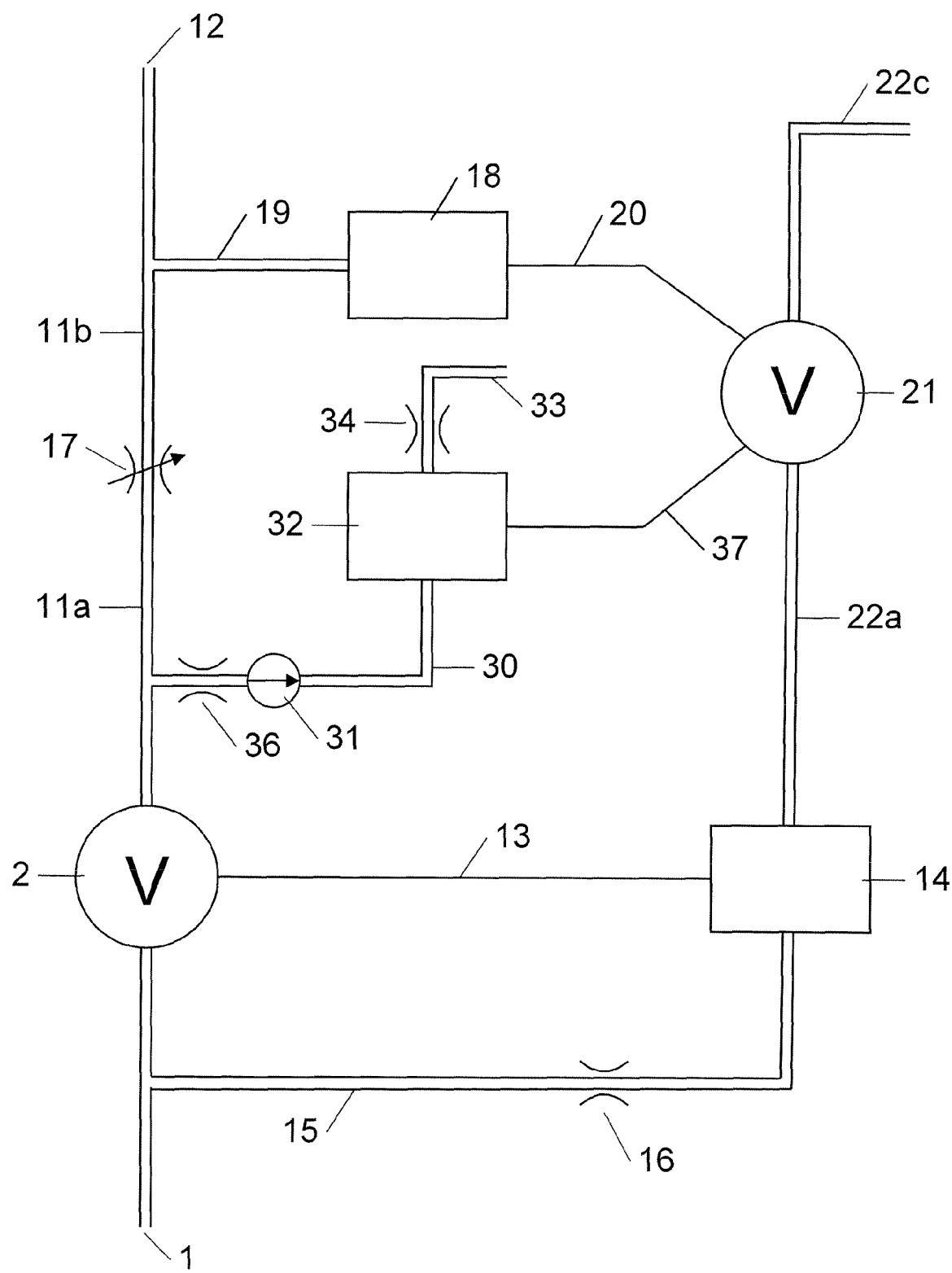
FIG. 6 is a block diagram of a third embodiment of an oxygen conserving device according to the invention.

Reference is now made to FIG. 6 which shows a third embodiment of the invention. The difference between the embodiment of FIG. 6 and the earlier embodiments is that the sensing delay volume 32 acts to control the sensing valve 21, instead of its own sensing delay valve. This is represented by the control line 37. Operation of the sensing delay valve 21 is thus under the control of the level of pressure in two volumes: the sensing volume 18 and the sensing delay volume 32. In FIG. 6, the emptying and filling of the various control volumes and operation of the valves is essentially the same as described previously, and only the differences will be discussed.

The sensing valve 21 is controlled by the pressure in sensing volume 18, via the control line 20, in the manner described above. The control line 37 exerts an overriding control, acting to inhibit operation of the valve, when the pressure in the sensing delay volume is greater than 10% of the supply pressure. Thus, when the output line 11*a* becomes pressurised to supply pressure at the beginning of the pulse of gas supplied to the user, the sensing delay volume pressurises via line 30 and one-way valve 31. When the pressure in volume 32 becomes greater than 10% of the supply pressure, the operation of the sensing valve 21 is inhibited via control line 37, and this situation continues, in the manner described previously, until the end of the predetermined period, during the subsequent exhalation. Thus, as before, the valve 21 remains closed, thus preventing the main control volume 14 from venting via the vent line 22.

There are various ways in which the control represented by control line 37 is exerted, and two will now be described with reference to the more detailed pneumatic circuit diagrams of FIGS. 7 and 8.

Figure 7:
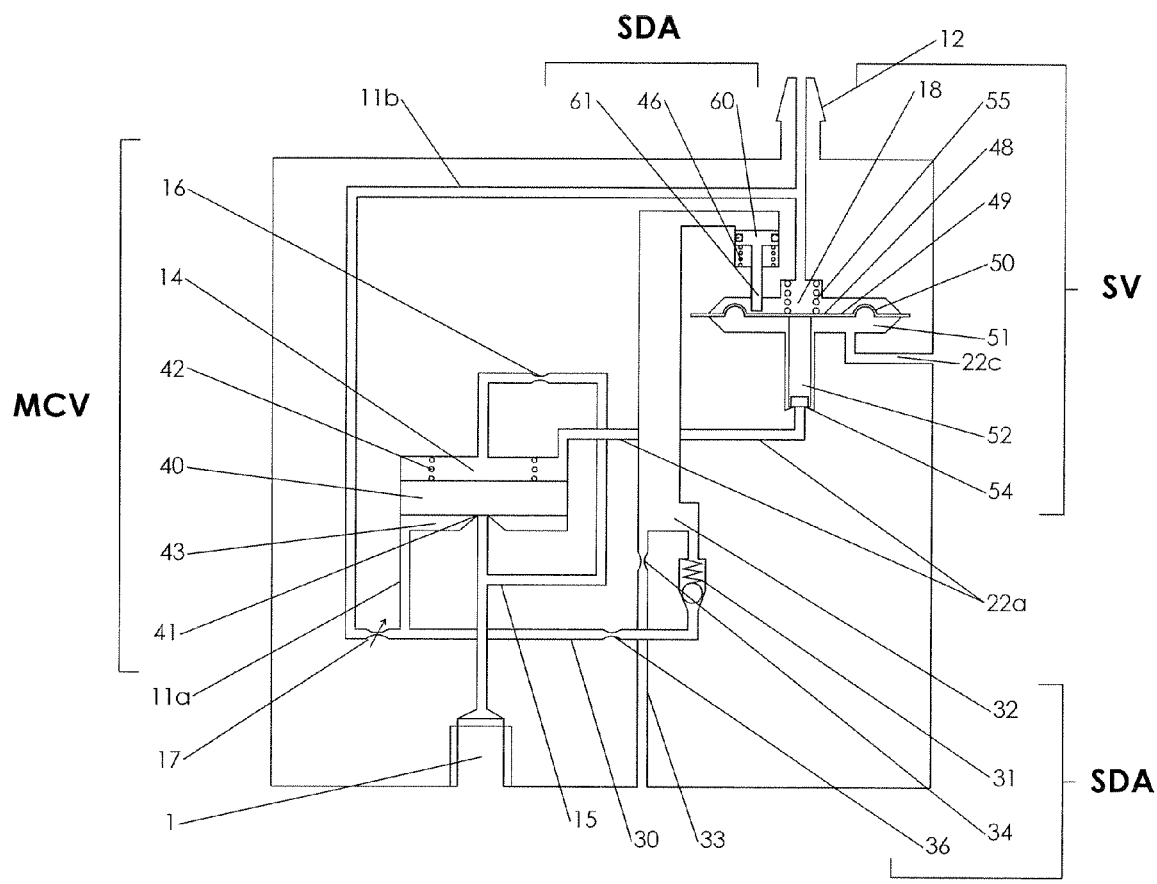
FIG. 7 is a more detailed pneumatic circuit diagram illustrating one way of implementing the embodiment of FIG. 6.

Referring firstly to FIG. 7, this will be seen to be similar to FIG. 3, with the principal exception that the sensing delay diaphragm 44 is replaced by a piston 60 to which is attached

TABLE 2

| No | Stage | Typ Time (s) | Pressures in the Volumes as Labelled in the Drawing FIG. 5 | | | | | State of Valves | | | Flow To User |
|---|---|---|---|---|---|---|---|---|---|---|---|
| | | | 43 | 14 | 32 | 18 | 47 | MCV | SLS | SV | |
| 1 | Ready state | — | 0 | 100% | 0 | 0 | 0 | closed | open | closed | 0 |
| 2 | Start inhale | 0 | 0 | 100% falling rapidly | 0 | ~−60 Pa | as 18 | closed | open | open | 0 |
| 3 | Pressure in 14 has fallen, MCV opens | 0.02 | Rising quickly to 100% | 10% or below | 0, rising quickly to 100% | Rising quickly to ~+10,000 Pa | as 18 | open | open, closing rapidly | open, closing rapidly | Flow |
| 4 | SV & SLS have shut | 0.05 | 100% | 10% rising | Rising | ~+10,000 Pa | as 18 | open | closed | closed | Flow |
| 5 | MCV just closing | 0.55 | 100% Falling | 90% rising | 100% | ~+10,000 Pa | as 18 | closing | closed | closed | Flow, falling |
| 6 | MCV just closed | 0.58 | Falling to 0 quickly | Rising to 100% | 100%, falling | ~+10,000 Pa | ~+10,000 Pa | closed | closed | closed | 0 |
| 7 | User still inhaling after stage 6 | 0.60 | 0 | 100% | Falling | ~−60 Pa | ~+10,000 Pa | closed | closed | closed | 0 |
| 8 | SLS opens, patient exhaling | 2 | 0 | Rising to 100% | 0 | + few mm H$_2$O | + few mm H$_2$O | closed | open | closed | 0 |
| 9 | Back to stage 1 | | 0 | 100% | 0 | 0 | 100% | closed | open | closed | 0 | a shaft 61 which extends externally of the cylinder into the sensing volume 18 of the sensing valve. It will be understood that the piston 60 could in practice be constituted by a diaphragm somewhat similar to diaphragm 44.

The piston 60 is biased by means of the spring 46 in such a way that the lower end of the shaft 61 is clear of the sensing diaphragm 48 and does not interfere with its normal operation. However, in response to pressure in the sensing delay volume 32, the piston 60 and shaft 61 can move downwards so that the lower end of the shaft 61 engages the diaphragm 48 and prevents it moving upwards in response to negative pressure in the output line 11b resulting from patients' inhalation. The jet 54 of the sensing valve thus remains closed and venting of the main volume 14 is prevented.

This situation continues until the sensing delay volume 32 has vented via vent line 33 and restriction 34 to an extent that the pressure within the volume 32 becomes less than 10% of the supply pressure. At this point, the lower end of the shaft 61 has risen sufficiently to allow the sensing diaphragm 48 to operate normally.

Figure 8:
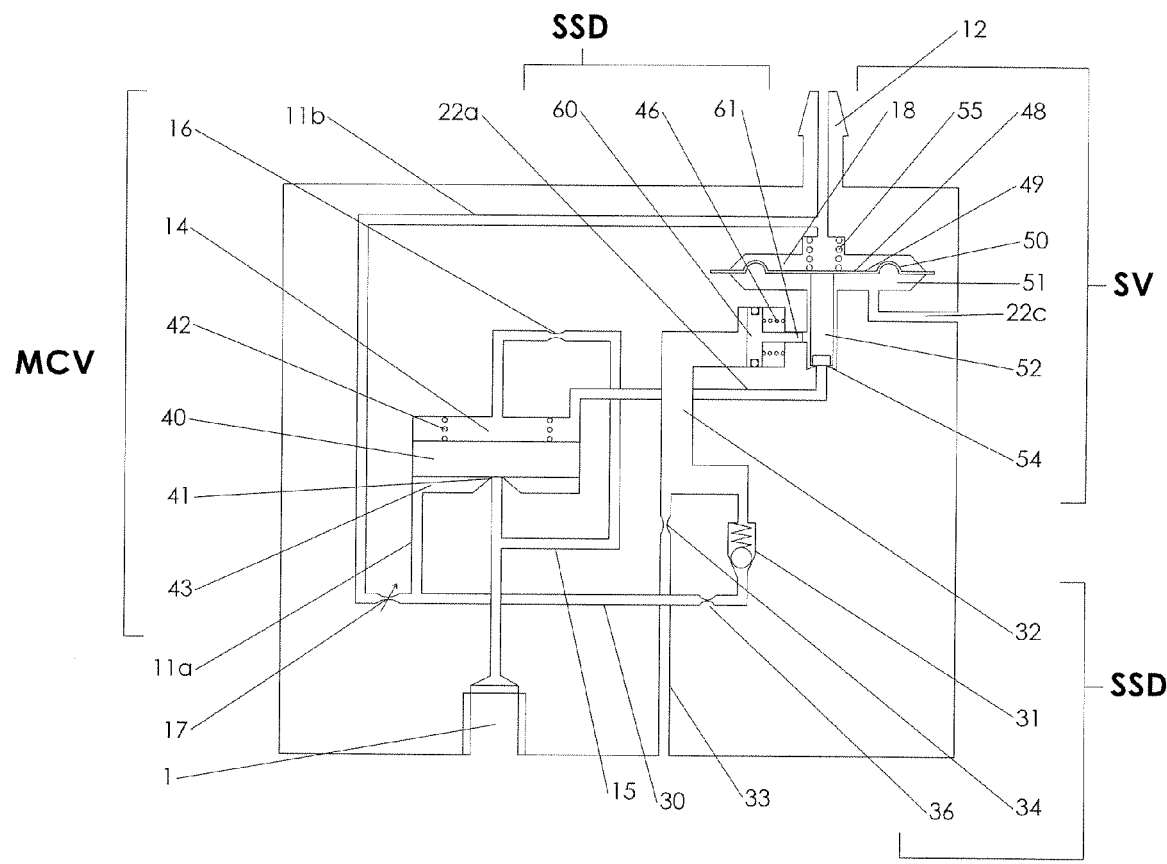
FIG. 8 is a more detailed pneumatic circuit diagram illustrating an alternative way of implementing the embodiment of FIG. 6.

Referring now to FIG. 8, this will be seen to be very similar to FIG. 7 with the exception that the shaft 61 of the piston 60 acts upon the valve stem 52.

In the position illustrated, the end of the shaft 61 is clear of the valve stem 52 and the sensing valve thus operates normally. In this condition, lifting of the diaphragm 48, due to inhalation by the user, causes the valve stem 52 to rise due to pressure within the vent line 22a. Gas within the vent line 22a thus escapes around the side of the valve stem into the chamber 51 and is vented to atmosphere via the vent line 22c. However, if the pressure in the sensing delay volume 32 rises above 10% of the supply pressure, the piston 60 and shaft 61 move sufficiently in the rightwards direction that the right-hand end of shaft 61 engages the valve stem 52 and prevents it from moving. This locks the valve stem 52 in a position in which it seals the jet 54, thus preventing venting of the main control volume 14 via the vent line 22a. This situation continues for as long as the pressure in the sensing delay volume 32 remains above 10% of the supply pressure and thus effectively inhibits the operation of the sensing valve during this period.

The operation of each of the embodiments of FIGS. 7 and 8 is essentially very similar, and can be summarised in the following table which gives the sequence of operation in each case, together with pressure and valve states at each stage. As before, the quoted percentages refer to percentages of the supply pressure. In the following table, when the piston 60 is described as up, this means that the shaft 61 is in a position where it does not affect operation of the sensing valve (SV); when the piston 60 is described as down, this means that the shaft 61 is in a position in which it prevents operation of the sensing valve.

TABLE 3

| No | Stage | Typ Time (s) | Pressures in the Volumes as Labelled in the Drawing FIGS. 7 and 8 | | | | State of Valves | | | Flow To User |
|---|---|---|---|---|---|---|---|---|---|---|
| | | | 43 | 14 | 32 | 18 | MCV | SDA | SV | |
| 1 | Ready state | — | 0 | 100% | 0 | 0 | closed | Piston 60 up | closed | 0 |
| 2 | Start inhale | 0 | 0 | 100% falling rapidly | 0 | ~−60 Pa | closed | Piston 60 up | open | 0 |
| 3 | Pressure in 14 has fallen, MCV opens | 0.02 | Rising quickly to 100% | 10% or below | 0, rising quickly to 100% | Rising quickly to ~+10,000 Pa | open | Piston 60 moving down | open, closing rapidly | Flow |
| 4 | SV & SDA have shut | 0.05 | 100% | 10% rising | Rising | ~+10,000 Pa | open | Piston 60 down | closed | Flow |
| 5 | MCV just closing | 0.55 | 100% Falling | 90% rising | 100% | ~+10,000 Pa | closing | piston 60 down | closed | Flow, falling |
| 6 | MCV just closed | 0.58 | Falling to 0 quickly | Rising to 100% | 100%, falling | ~+10,000 Pa Falling to 0 | closed | piston 60 down | closed | 0 |
| 7 | User still inhaling after stage 6 | 0.60 | 0 | 100% | Falling | ~−60 Pa | closed | piston 60 down | closed | 0 |
| 8 | SDA opens, user exhaling | 2 | 0 | Rising to 100% | 0 | + few mm H$_2$O | closed | piston 60 moving up | closed | 0 |
| 9 | Back to state 1 | | 0 | 100% | 0 | 0 | closed | piston 60 up | closed | 0 |

The invention claimed is:

1. A pneumatically-controlled pneumatic conserving device for breathable gas, the device comprising:
   a pneumatically-controlled main control valve connected in a user supply line between an inlet for receiving a supply of breathable gas and an outlet for connection to a user,
   a main valve timer, comprising a main control volume, the pressure within the volume controlling the opening and closing of the main control valve, and
   a sensing valve for triggering the main valve timer to open the main control valve upon sensing inhalation by the user, and to deliver a pulse of gas of predetermined duration to the outlet,
   the device being characterised by a pneumatically-operated sensing valve inhibitor for inhibiting operation of the sensing valve, the inhibitor comprising:
   a sensing delay volume, the pressure within which controls operation of the inhibitor, a cylinder in which is situated a moveable member, the sensing delay volume being to one side of the moveable member;

a delay line through which the sensing delay volume is pressurized by gas flow when the main control valve is open, and a delay timer comprising a flow restrictor and vent line connected to the sensing delay volume for controlling the sensing valve inhibitor to inhibit operation of the sensing valve for a predetermined period following the delivery of the pulse of gas to the outlet.

2. A conserving device as claimed in claim 1 wherein the delay line includes a one-way valve allowing flow into the sensing delay volume, but not in the reverse direction.

3. A conserving device as claimed in claim 2 further including a flow metering valve connected in the user supply line on the downstream side of the main control valve, and wherein the delay line is connected to the user supply line at a point between the main control valve and the flow metering valve.

4. A conserving device as claimed in claim 1 wherein the delay line is connected to the user supply line at a point downstream of the main control valve so as to enable the sensing delay volume to be pressurised from the user supply line.

5. A conserving device as claimed in claim 1 wherein the cylinder includes a biasing element for biasing the moveable member in a direction such as to reduce the capacity of the sensing delay volume.

6. A conserving device as claimed in claim 1 wherein the moveable member takes the form of a diaphragm.

7. A conserving device as claimed in claim 1 wherein the moveable member takes the form of a piston.

8. A conserving device as claimed in claim 1 wherein the vent line is arranged to vent the sensing delay volume to atmosphere.

9. A conserving device as claimed in claim 1 wherein the vent line is arranged to vent the sensing delay volume into the user supply line downstream of the main control valve.

10. A pneumatically-controlled pneumatic conserving device for breathable gas, the device comprising:

a pneumatically-controlled main control valve connected in a user supply line between an inlet for receiving a supply of breathable gas and an outlet for connection to a user, a main valve timer, comprising a main control volume, the pressure within the volume controlling the opening and closing of the main control valve, and a sensing valve for triggering the main valve timer to open the main control valve upon sensing inhalation by the user, and to deliver a pulse of gas of predetermined duration to the outlet, the sensing valve being connected to the main control volume in such a way as to rapidly change the pressure in the volume in order to open the main control valve to supply gas to the user upon the sensing valve sensing inhalation by the user the device being characterised by a pneumatically-operated sensing valve inhibitor for inhibiting operation of the sensing valve, the inhibitor comprising:

a sensing delay valve and control comprising a moveable member, a sensing delay volume, the pressure within which controls operation of the inhibitor, the control being arranged to close the sensing delay valve as it moves when the pressure in the sensing delay volume rises above a first predetermined level, and to open the valve as it moves when the pressure in the sensing delay volume falls below a second predetermined level, a delay line through which the sensing delay volume is pressurized by gas flow when the main control valve is open, and a delay timer comprising a flow restrictor and vent line connected to the sensing delay volume for controlling the sensing valve inhibitor to inhibit operation of the sensing valve for a predetermined period following the delivery of the pulse of gas to the outlet.

11. A conserving device as claimed in claim 10 wherein the sensing valve further includes a sensing volume, a connection between the sensing volume and a user, and a control for opening the sensing valve when the pressure in the sensing volume is negative, indicating inhalation by the user.

12. A conserving device as claimed in claim 11 wherein the connection comprises a line connecting the sensing volume to the user supply line.

13. A conserving device as claimed in claim 11 for connection to a twin-tube cannula, wherein the connection comprises means for connecting the sensing volume to one tube of the twin-tube cannula, and the outlet is connected to the other tube of the twin-tube cannula.

14. A conserving device as claimed in claim 11 wherein the sensing delay valve is connected between the user supply line and the sensing volume so that, when closed, the sensing delay valve prevents the sensing valve from sensing the pressure in the user supply line.

15. A conserving device as claimed in claim 10 wherein the sensing delay valve is connected between the main control volume and the sensing valve so that, when closed, the sensing delay valve isolates the sensing valve and prevents it from changing the pressure in the main control volume.

16. A conserving device as claimed in claim 10 wherein the inhibitor comprises an inhibiting member which is moveable between a first position, in which it prevents operation of the sensing valve, and a second position in which it does not prevent operation of the sensing valve, according to the pressure within the sensing delay volume.

17. A conserving device as claimed in claim 16 wherein the inhibiting member is linked to the moveable member so that, as the pressure in the sensing delay volume changes, the moveable member moves and causes movement of the inhibiting member from its first to its second position, and vice versa.

* * * * *

UNITED STATES PATENT AND TRADEMARK OFFICE
CERTIFICATE OF CORRECTION

PATENT NO. : 8,276,584 B2
APPLICATION NO. : 11/817557
DATED : October 2, 2012
INVENTOR(S) : Tatarek Page 1 of 1

It is certified that error appears in the above-identified patent and that said Letters Patent is hereby corrected as shown below:

Column 7,
Line 26, "line 22" should read --line 22*a*--.

Column 11,
Line 59, "line 22" should read --line 22*a*--.

Signed and Sealed this
Nineteenth Day of March, 2013

Teresa Stanek Rea
*Acting Director of the United States Patent and Trademark Office*